United States Patent [19]

Li et al.

[11] 4,264,531

[45] Apr. 28, 1981

[54] LIQUID, LINEAR PHOSPHAZENE PREPOLYMERS AND PROCESS FOR PREPARING SAME

[75] Inventors: Hsueh M. Li; Edwin D. Hornbaker, both of Baton Rouge, La.

[73] Assignee: Ethyl Corporation, Richmond, Va.

[21] Appl. No.: 94,344

[22] Filed: Nov. 14, 1979

[51] Int. Cl.³ .................................................. C07F 9/00
[52] U.S. Cl. .................................. 260/926; 260/973; 521/189; 528/168
[58] Field of Search ................................. 260/926, 973

[56] References Cited

U.S. PATENT DOCUMENTS

| | | | |
|---|---|---|---|
| 3,443,913 | 5/1969 | Bienick et al. ........................ 23/357 |
| 3,676,311 | 7/1972 | Frank et al. ........................... 260/926 |
| 3,856,713 | 12/1974 | Rose ....................................... 260/2 P |
| 4,107,146 | 8/1978 | Dieck et al. ........................... 528/168 |
| 4,116,785 | 9/1978 | Cheng .................................. 204/159.14 |

FOREIGN PATENT DOCUMENTS 50-82041  3/1975  Japan ........................................ 260/926

*Primary Examiner*—Anton H. Sutto
*Attorney, Agent, or Firm*—Donald L. Johnson; John F. Sieberth

[57] ABSTRACT

Substituted, linear phosphazene prepolymers and processes for their preparation are disclosed. These prepolymers are liquid at ambient temperatures and can be conveniently cured and/or foamed without the use of external heat.

18 Claims, No Drawings

LIQUID, LINEAR PHOSPHAZENE PREPOLYMERS AND PROCESS FOR PREPARING SAME

This invention relates to liquid, linear phosphazene prepolymers. More particularly, it relates to substituted, crosslinkable pleionomeric phosphazenes which can be readily cured and foamed at ambient temperatures, and to processes for their preparation.

BACKGROUND

Various curable and foamable phosphazene polymers have been disclosed in the prior art. For example, U.S. Pat. No. 3,856,713 describes the preparation of elastomeric poly(aryloxyphosphazene) copolymers. Because these copolymers are solid, fabrication of products therefrom, e.g., by foaming, requires high temperatures. Furthermore, these copolymers are crosslinked by conventional methods requiring high temperatures or use of radiation, such as peroxide curing and sulfur curing (vulcanization).

U.S. Pat. No. 4,107,146 discloses cured phosphazene polymers substituted with aryloxy groups and a group capable of a crosslinking chemical reaction (such as an alkenyl substituted aryloxy) and the process for curing. These polymers are solid at room temperature and are crosslinked at elevated temperatures with conventional sulfur curing agents such as sulfur monochloride. The solid polymers must be heated to between 200° F. and 350° F. in order to be foamed.

U.S. Pat. No. 4,116,785 discloses phosphazene polymers substituted with alkoxy and aryloxy groups and with from 0.1 to 5 percent of the total substituents having olefinic unsaturation. These polymers are solid at room temperature. They are cured by conventional curing agents and require heating to about 300° F. in order to be cured.

U.S. Pat. No. 3,676,311 discloses burn-resistant polymers prepared by photocuring a mixture of polythiol and a phosphonitrilic polymer containing at least two reactive unsaturated carbon-to-carbon groups. Solid and liquid cross-linkable polymers are produced and used in this manner. Some of them are cyclic polymers; others are linear. In preparing these polymers all or part of the halide atoms of a phosphonitrilic halide, preferably in cyclic form, are replaced by unsaturated groups, such as allyloxy and the like.

When preparing foams or crosslinked products it is desirable that the crosslinkable prepolymer be in liquid form at ambient temperatures as this facilitates handling and use.

THE INVENTION

In accordance with the present invention there is provided a liquid, linear, crosslinkable prepolymer, viz., a polymeric phosphazene having an average degree of polymerization of from about 20 to about 70 (and preferably, from about 20 to about 50) wherein substantially all of the substituents on said phosphazene are —OR, —SR, —NHR', —NR$_2$ or mixtures thereof in which R is an organic radical having no more than about 10 carbon atoms and R' is an organic radical having from 2 to 10 carbon atoms; the prepolymer being further characterized in that from about 8% to about 50% of the total number of the substituents have at least one site of crosslinkable ethylenic unsaturation, in that at least 50% of the substituents are —OR groups, in that no more than 25% of the substituents are aromatic and in that the prepolymer has a viscosity of not more than 500,000 centipoises at 23° C. It will be seen that about 8 to about 50% of the substituents have organic groups (i.e., R and R' groups) which contain olefinic unsaturation, the organic groups of the remainder of the substituents being paraffinic, cycloparaffinic, and optionally, aromatic with the proviso that not more than 25% of all of the substituents contain aromatic groups. Preferably the organic radicals, R and R', of the substituents of the crosslinkable prepolymers of this invention are all open chain (i.e., non-cyclic) organic radicals. It will also be seen that at least one-half of all of the substituents are bonded to the linear phosphazene chains by means of an oxygen atom.

From a structural point of view, the prepolymers of this invention are composed of linear phosphazene chains the phosphorus atoms of which are bonded to the above substituents in the appropriate proportions as specified. The differing substituents are normally randomly positioned along the polymeric chains.

Among the particularly preferred phosphazenes of this invention are those wherein from 8 to 25% of the substituents are diallylamino and 92 to 75% (i.e., the balance) of the substituents are alkoxy of from 1 to 4 carbon atoms, most preferably n-butoxy; those wherein from 10 to 35% of the substituents are allyloxy and 90 to 65% of the substituents are alkoxy of from 1 to 4 carbon atoms, most preferably n-butoxy; and those wherein from 10 to 35 percent of the substituents are methacryloyloxyethoxy and 90 to 65 percent of the substituents are alkoxy of from 1 to 4 carbon atoms, most preferably n-butoxy.

Other preferred embodiments of this invention include the above described polymeric phosphazene prepolymers in admixture with up to about 25 phr of a polythiol curing agent or a polyacrylate curing agent. In still other embodiments, the prepolymers are in admixture with up to about 25 phr of a viscosity depressing agent—i.e., a substance further increasing the fluidity of the above crosslinkable polymeric polyphosphazenes.

To prepare the substituted phosphazenes of the present invention use may be made of several processes, the choice of which is governed to some extent by the substituents desired on the liquid, prepolymeric product. These processes involve the reaction of a linear phosphonitrilic chloride pleionomer having an average degree of polymerization of from about 20 to about 70 (preferably 20 to 50) with other reactants. One such process, sometimes referred to herein as the salt process, involves reacting these pleionomers in admixture with an alkali metal alkoxide reactant having up to about 10 carbon atoms in the molecule, an alkali metal alkenoxide reactant having up to about 10 carbon atoms in the molecule and optionally, an alkali metal phenoxide reactant also having up to about 10 carbon atoms in the molecule. These reactants are used in amounts so that the alkenoxide furnishes from about 8 to about 50% of the total number of substituents formed by replacement of chlorine from the pleionomer. The alkali metal phenoxide, if used, is used in amounts so that no more than 25% of the substituents formed by replacement of chlorine from the pleionomer are furnished by this phenoxide. In this process the balance of the substituents on the pleionomers of this invention is furnished by the alkali metal alkoxide reactant.

Another method for preparing the prepolymers of this invention, sometimes referred to herein as the alkenylamine process is a 2-step process. In the first step, the linear phosphonitrilic chloride pleionomer is reacted with a primary or a secondary alkenylamine, e.g. a dialkenylamine, reactant having up to about 10 carbon atoms to effect partial substitution of the pleionomer. These amines are reacted in amounts so that from about 8 to about 50% of the chlorine atoms on the pleionomer are replaced by a primary or a secondary monoalkenylamino or dialkenylamino group. In the second step of the alkenylamine process, the partially substituted pleionomer is reacted with an alkali metal alkoxide reactant having up to about 10 carbon atoms in the molecule and optionally, with an alkali metal phenoxide also having up to about 10 carbon atoms in the molecule so that substantially all of the remaining chlorine atoms on the partially substituted pleionomer are replaced by alkoxy and optionally, phenoxy groups. As in the salt method, the alkali metal phenoxide, when employed is used in amounts so that no more than 25% of the chlorine atoms of the initial phosphonitrilic chloride pleionomer are replaced by phenoxy groups.

In still another method for the preparation of the substituted pleionomers of this invention, referred to herein as the alcohol/amine process, a 2-step reaction sequence is also employed. In the first step of the sequence the phosphonitrilic chloride pleionomers are reacted in the presence of a tertiary amine with a reactant such as an hydroxyalkyl acrylate, an hydroxyalkyl methacrylate, and hydroxyalkyl acrylamide or an hydroxyalkyl methacrylamide, each having no more than up to about 10 carbon atoms in the molecule. The amounts of these reactants used are selected so that from about 8 to about 50% of the chlorine atoms on the phosphonitrilic chloride pleionomers are replaced by acryloylaminoalkoxy methacryloylaminoalkoxy, acryloyloxyalkoxy or methacryloyloxy alkoxy groups thereby forming partially substituted phosphonitrilic chloride pleionomers. These partially substituted pleionomers are then reacted, again in the presence of a tertiary amine, with an alkanol reactant having up to about 10 carbon atoms in the molecule, and optionally, a phenol reactant also having up to about 10 carbon atoms in the molecule. The amounts of these reactants are selected so that substantially all of the remaining chlorine atoms of the partially substituted pleionomers are replaced by alkoxy and optionally, phenoxy groups. As in the salt and the alkenylamine processes, when an alkali metal phenoxide is employed it is used in amounts such that no more than about 25% of the chlorine atoms of the initial phosponitrilic chloride pleionomers are replaced by phenoxy groups.

Variations in or modifications of the foregoing processes can also be used. For example, to introduce saturated aliphatic, saturated cycloaliphatic or aromatic groups into the pleionomer modifications may be made in the alkenylamine process. Thus in the first step a combination of an alkenylamine and a saturated aliphatic, saturated cycloaliphatic or aromatic amine may be utilized to form a partially substituted pleionomer. Thereupon, the second step of the alkenylamine process may be conducted as described above. Alternatively the first step of the alkenylamine process may be altered so that only a saturated aliphatic, saturated cycloaliphatic or aromatic amine is utilized in the appropriate proportions to yield a partially substituted pleionomer in which the substituents are all saturated aliphatic amino, saturated cycloaliphatic amino or aromatic amino groups. Thereupon, the second step of the process is modified so that in addition to an alkali metal alkoxide (and optionally an alkali metal phenoxide) an alkali metal alkenoxide is used so as to introduce the requisite content of alkenyl unsaturation in the pleionomer. Still other variants will now be apparent to those skilled in the art.

Regardless of the method employed, it is an aspect of this invention that the resulting fully substituted, linear polymeric phosphazenes have viscosities of no more than 500,000 cps at 23° C.

A variety of compounds find use as reactants in the preparation of the liquid prepolymers of this invention. When a phosphonitrilic chloride backbone is used, the reactants replace the two labile chlorine atoms on each phosphorus atom to form the corresponding —OR, —SR, —NHR' and —NR$_2$ substituents on the phosphazene backbone.

The reactants which form the —OR substituents are those having the formula ROH and ROM wherein R is an organic radical having up to about 10 carbon atoms and M is an alkali metal, preferably sodium. Thus these reactants include alcohols, phenols, alkali metal alcoholates and alkali metal phenolates. Examples of suitable monohydric saturated aliphatic alcohols include methanol, ethanol, n-propanol, isopropanol, n-butanol, sec-butanol, 2-hexanol, 2-methoxyethanol, 2,2,2-trifluoroethanol, 1-decanol, and the alkali metal salts thereof; suitable cycloaliphatic alcohols include cyclohexanol, cyclobutanol, cyclobutanemethanol, 2-chlorocyclohexanol, 4-methylcyclohexanol, cyclodecanol and the alkali metal salts thereof; suitable phenolic compounds and arylaliphatic alcohols include phenol, o-methoxyphenol, m-methoxyphenol, p-methoxyphenol, o-cresol, m-cresol, p-cresol, o-ethylphenol, m-ethylphenol, p-ethylphenol, m-propylphenol, o-chlorophenol, m-chlorophenol, p-chlorophenol, o-bromophenol, m-bromophenol, p-bromophenol, 2-bromo-4-hydroxytoluene, 2,4,6-trichlorophenol, 2,4,6-tribromophenol, 4-chloro-3-methylphenol, p-tert-butyl phenol, benzyl alcohol, 2-bromo-benzyl alcohol, p-nitrobenzyl alcohol, p-ethylbenzyl alcohol and the alkali metal salts thereof. Ethylenically unsaturated alcohols which find use herein include allyl alcohol, 3-buten-1-ol, 3-buten-2-ol, 2-methyl-2-propene-1-ol (methallyl alcohol), 2-allyloxyethanol, 2-allyloxypropanol, 2,3,3-trifluoro-2-propene-1-ol, 4-hydroxybutyl vinyl ether, 1-octene-8-ol, 2-octene-4-methyl-8-ol, 4-allyloxybutanol and the alkali metal salts thereof. Suitable hydroxyalkyl acrylates, methacrylates, acrylamides and methacrylamides include 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, N-(2-hydroxyethyl) acrylamide, N-2-hydroxyethyl) methacrylamide, N-(hydroxymethyl)acrylamide, N-(2-hydroxypropyl) methacrylamide, N-(3-hydroxypropyl) methacrylamide, N-(2-hydroxyethyl) bromo-methacrylamide and the alkali metal salts thereof. Alkenyl phenols which may be used include 2-allylphenol, 2-allyl-4-methylphenol, 2-allyl-6-methylphenol, 4-allyl-2,6-dimethoxy phenol, 2-vinylphenol, 4-vinylphenol, 4-allyl-2-methoxyphenol, 2-vinyl-4-bromophenol, 4-nitro-2-vinylphenol, 4-(3-butenyl)phenol and the alkali metal salts thereof.

The reactants which form the —SR substituents are those having the formula RSH and RSM wherein R is an organic radical having up to about 10 carbon atoms and M is an alkali metal, preferably sodium or potassium, most preferably sodium. Accordingly, these mono-functional reactants include aliphatic, cycloaliphatic and aromatic thiols (mercaptans) and the alkali metal salts thereof. Exemplary thiols include ethyl mercaptan, isopropyl mercaptan, heptyl mercaptan, nonyl mercaptan, cyclohexyl mercaptan, allyl mercaptan, thiophenol, p-thiocresol, 4-bromothiophenol, 4-bromo-m-thiocresol, 4-nitrothiophenol, benzyl mercaptan, 4-chlorobenzyl mercaptan, furfuryl mercaptan, and the like. The corresponding alkali metal salts may also be used.

The reactants which form the —NHR' and —NR$_2$ substituents are those having the formula R'NH$_2$ and R$_2$NH wherein R is an organic radical having up to about 10 carbon atoms and R' is an organic radical having from 2 to about 10 carbon atoms. Examples of these reactants include diethylamine, methylallylamine, ethylamine, isopropylamine, n-propylamine, n-butylamine, decylamine, cyclopropylamine, piperidine, ethylallylamine, butylallylamine, diallylamine, aniline, N-allylaniline, N-methylaniline, o-, m- and p-toluidine, the trichloroanilines, 3,4,5-trimethoxyaniline, 2,4,6-trimethylaniline, o-, m- and p-bromoaniline, p-butylaniline, o-, m- and p-nitroaniline, and the like.

Selection of reactants in production of the liquid phosphazenes of this invention will vary according to such factors as the particular substitution reaction used and the desired physical properties of the phosphazene product. Accordingly, in the salt process the ROM and RSM reactants hereinabove described are normally used to effect substantially complete substitution on the phosphonitrilic chloride pleionomer. In the first step of the alkenylamine process, a secondary alkenyl amine is used and in the second step a reactant of the formula ROM or RSM supplies the substituents which replace substantially all of the remaining chlorine atoms on the phosphazene chain. The alcohol/amine process (both steps of which are carried out in the presence of a tertiary amine) generally involves reacting the phosphonitrilic chloride pleionomer with an alcohol (saturated or unsaturated), preferably an hydroxyalkyl acrylate or methacrylate or N-(hydroxyalkyl) acrylamide or methacrylamide in order to effect the degree of substitution desired, the partially substituted pleionomer then being reacted with a compound of the general formula ROH, RSH, R'NH$_2$, R$_2$NH or mixtures thereof in order to effect substantially complete replacement of the partially substituted pleionomer. Naturally the reactants are proportioned so as to furnish the various substituents in the requisite proportions on the final product.

The salt process is usually conducted at temperatures between about 30° C. and 180° C., preferably between about 60° C. and 110° C. Preferably a suitable insert solvent or diluent is used. Examples of such reaction media include hydrocarbons such as hexane, heptane, ligroin, cyclohexane, benzene, toluene, xylene and the like, chlorinated aromatic hydrocarbons, for example, monochloro- and dichlorobenzene and the like, and linear or cyclic ethers such as diethyl ether, tetrahydrofuran and dioxane, and the like.

Preferably the phosphonitrilic chloride pleionomer is added to the reaction mixture containing the alkali metal compounds, ROM and/or RSM. The pleionomer is normally added over a period of time of between about 0.1 and about 10 hours, preferably between about 0.5 and about 3 hours.

In this process, the amount of each reactant used falls roughly in the range of the molar ratio of substitution desired. For example, if a 2:1 molar ratio of n-butoxy: allyloxy substituents is desired, roughly a 2:1 molar ratio of sodium butoxide: sodium allyloxide is used. The substitution reaction is rapid and exothermic at the beginning but the rate begins to drop off as more pleionomer is added. After the total amount of pleionomer has been added, heating is usually continued for a period ½ to about 8 hours thereafter in order to ensure complete substitution. If the substitution is less than substantially complete (i.e., at least about 99% of the chlorine functionality has been substituted) the resultant reaction mass can be heated and held at reflux temperature until analysis indicates substantially complete substitution of the pleionomer. After the substitution reaction is complete the substituted pleionomer can be isolated from the unreacted substituent reactants and from the solvent. Methods known in the art for isolation of a product, e.g., distillation, centrifugation and precipitation, may be used. The excess substituent and the solvent may then be recycled for later use. If desired, the sequence of addition of reactants may be reversed.

The first step of the alkenylamine process is preferably carried out at temperatures in the range of from about 20° C. to about 70° C. and is therefore a desirable reaction for placing substituents which may be sensitive to higher temperatures (e.g., undesired crosslinking and self polymerization) onto the phosphazene. Preferred solvents are those inert to the reactants and include those set forth in the salt process above. The amine reactant is usually added slowly over a period of from one to four hours and the mixture is then allowed to react for up to 25 hours or until the desired degree of substitution is obtained. The partially substituted pleionomer is then reacted with a reactant of the formula ROM and optionally RSM to complete replacement of the remaining chlorine atoms on the phosphonitrilic chloride. This second step substitution reaction is preferably carried out at between 40° and 90° C., most preferably between about 60° and 80° C. Usually this reaction is performed in a reaction solvent, preferably that used in the first step. A slight excess of moles of reactant(s) needed to complete substantial substitution is used in the reaction with the partially substituted pleionomer.

The alcohol/amine process entails contacting the phosphazene pleionomer with an alcohol or phenol in the presence of a tertiary amine which serves as an acid acceptor. Thus any of a wide variety of tertiary amines can be used, including, for example, triethylamine, triphenylamine, N,N-dimethylaniline, pyridine, and the like. Preferably the tertiary amine is used in greater than stoichiometric quantities relative to the HCl formed in the substitution reaction. The reactants and the amine may be dissolved in a suitable solvent such as toluene, or the amine itself may be used as the solvent. The temperature is generally kept between about 10° C. and 60° C. until the desired partial substitution is effected. When reactants such as the acrylates, methacrylates, acrylamides and methacrylamides are used, the preferred reaction temperatures fall within the range of from about 25° to about 40° C. After the first step has been completed the partially substituted pleionomer is reacted with another alcohol and optionally phenol in the presence of excess tertiary amine, preferably at a temperature between 40° and 70° C. Preferably the partially substituted pleionomer is isolated before being subjected to the second step reaction. The sequence may be repeated as often as desired.

The following examples will serve to illustrate specific embodiments of the present invention.

EXAMPLE 1 a. Preparation of Sodium Butoxide and Sodium Allyloxide

A five-liter, four-necked round bottom flask, was fitted with a heating mantle, a mechanical stirrer, a reflux condenser, an additional funnel and a thermometer. A mixture of one-liter of toluene and 45 g (1.95 moles) of sodium was charged to the flask which was then heated to about 100°–105° C. and stirred until the sodium melted and dispersed under vigorous stirring into fine droplets. The stirrer and heating system was then turned off to allow the contents to cool to about 50° C. After the sodium droplets settled the toluene was decanted and 1.2 liters of tetrahydrofuran (THF) was added. The sodium was again stirred in the THF and 159 g (2.15 moles) of n-butanol were added over a period of 2 hours. The mixture was then refluxed overnight and then cooled.

The sodium salt of allyl alcohol was prepared in a similar fashion. In this case a two-liter, four-necked round bottom flask was used and 24.2 g (1.05 moles) of sodium were melted and divided in 800 ml of toluene at about 100°–105° C. After the toluene was decanted, one-liter of THF and 71.5 g (1.23 moles) of allyl alcohol were added over a 2 hour period. The mixture was refluxed overnight and then allowed to cool.

b. Preparation of Allyloxy-Butoxy Substituted Prepolymer

The suspensions of sodium allyloxide and sodium butoxide in THF were mixed in a five-liter flask. In another flask, 174 g of linear $PNCl_2$ pleionomer having a number average molecular weight ($\overline{M}_n$) of 7300 was dissolved in toluene. This solution was then added to the mixture of sodium allyloxide and butoxide over a period of 2 hours. The resulting mixture was then refluxed while being stirred at 66°–67° C. for 48 hours. The resulting allyloxy-butoxy substituted crosslinkable prepolymer was stripped of 1.2 liters of THF leaving a turbid suspension. The suspension was then added to a large volume of water and neutralized with HCl solution. The aqueous phase was decanted and the organic phase was centrifuged and the centrifugate was then evaporated to dryness to yield 213 g (75.5% yield) of viscous prepolymer at room temperature.

A subsequent proton NMR analysis of the product indicated that relative mole percent of the allyloxy:n-butoxy substituents to be 34.3:65.7 respectively. The viscosity of the viscous prepolymer was then measured with a Brookfield Viscometer and was found to have a viscosity of 340,000 cps. at 23° C.

EXAMPLE 2

Preparation of Diallylamino-Butoxy Substituted Prepolymer

A one-liter, four-necked round bottom flask was fitted with a heating mantle, a mechanical stirrer, an addition funnel, a condenser and a thermometer. A mixture of 58 g (0.5 moles) of linear $PNCl_2$ pleionomer ($\overline{M}_n \cong 4,000-5,000$) dissolved in 80 ml of toluene was charged along with 200 ml of toluene to the flask and stirred. 21.7 g (0.223 moles) of diallylamine were slowly added from the addition funnel over a period of 2 hours. During the initial stages of introduction of the diallylamine, $N_2$ gas was swept across the liquid surface in order to clear out a fog formed during the reaction. This mixture was then stirred at 55°–60° C. for 15 hours. The mixture was then cooled to room temperature and the partially substituted phosphonitrilic chloride pleionomer was separated from the diallylamine hydrochloride by-product by filtration and subsequent washing with fresh toluene. 14.6 g (0.11 moles) of the diallylamine hydrochloride were obtained. The filtrate was stored in a sealed container.

The sodium salt of n-butanol was then prepared in a five-liter, four-necked round bottom flask equipped with a mechanical stirrer, a condenser, an additional funnel and a thermometer. 23 g (1 g-atom) of sodium and 1500 ml of toluene were heated to 95°–100° C. in the round bottomed flask with continuous stirring. When the sodium melted into fine droplets, 78.6 g (1.06 moles) of n-butanol were added over a period of 2 hours. The mixture was stirred at 95°–100° C. for an additional hour and then cooled down to 70° C.

At this point the diallylamine partially substituted phosphonitrilic chloride pleionomer filtrate prepared as described in the first paragraph of this example was added over a period of 10–20 minutes into the reaction flask containing the sodium butoxide. This reaction mixture was kept at 75°–80° C. with stirring over a 14 hour period. The resulting reaction mixture was then transferred into a distilling flask where about one-liter of toluene was stripped off under vacuum at 50° C. The residue was added to a large volume of water and separated into layers in a separatory funnel. The lower, aqueous layer was discarded and the upper layer containing the substituted prepolymer was then heated to 60° C. to remove the residual toluene. The crude paste-like product was then washed with water until a neutral pH reading was obtained. The dried product was 80 g (78% yield) of a pourable paste-like diallyalmino n-butoxy substituted prepolymer. The viscosity of this prepolymer was found to be 66,000 cps at 23° C. as measured by a Brookfield Viscometer. A subsequent proton NMR analysis of the product indicated the relative mole percent of the two substituents to be as follows:

12.2 mole-percent of diallylamino substituent 87.8 mole-percent of n-butoxy substituent.

The prepolymer had a number average molecular weight ($\overline{M}_n$) of 6,900.

EXAMPLE 3

Preparation of Methacryloyloxyethoxy-Butoxy Substituted Prepolymer

A solution of 0.5 moles (58 g) of linear $PNCl_2$ pleionomer (having an $\overline{M}_n$ of about 5,000) in 80 ml toluene and 9.8 g (0.075) mole of 2-hydroxyethyl methacrylate were dissolved in 200 ml of tetrahydrofuran (THF) in a two-liter, four-necked round bottom flask. To the stirred solution, 25.3 g (0.25 mole) of triethylamine were slowly added from the addition funnel at ambient temperature over a period of one hour. The mixture was then stirred for 4 hours at 45° C. and the resulting precipitated triethylamine hydrochloride salt (10 g, 0.073 mole) was removed by filtration. This quantity of collected salt indicated that the 2-hydroxyethyl methacrylate was essentially completely reacted. The filtrate was poured back into the same reaction flask and 150.2 g (2.02 mole) of n-butanol was added. After 404 g (4.0 mole) of triethylamine was added over a two hour period the temperature was raised to 63°–65° C. and the substitution reaction carried out over a period of 60 hours at this temperature and for another 20 hours at ambient temperature. The precipitated triethylamine hydrochloride salt (79.5 g, 0.577 mole) was removed by filtration and the filtrate condensed to approximately 225 ml by evaporation of the THF solvent. The condensed residue was added to one-liter of methanol/H$_2$O (1:1 volume/volume) mixture to precipitate the methacryloyloxyethoxy-butoxy substituted prepolymer. The upper, methanol-water layer was decanted and the paste-like bottom layer comprising the prepolymer was washed twice with 200 ml of methanol and then dried to yield approximately 30 g of syrup-like material. The viscosity of the prepolymer was measured with a Brookfield Viscometer and was found to be 40,000 cps at 23° C. A subsequent proton NMR analysis of this same prepolymer indicated a relative mole percent of the two substituents to be as follows:

14 mole-percent of methacryloyloxyethoxy substituent
86 mole-percent of n-butoxy substituent.

The phosphonitrilic chloride pleionomeric starting material, used in each method set forth hereinabove in making the liquid products of this invention, is well known in the art. For example, U.S. Pat. No. 3,443,913 discloses a method wherein linear (PNCl$_2$)$_{3\text{-}15}$ oligomers are heated at 240°–260° C. to produce linear phosphonitrilic chloride pleionomers having a molecular weight between 3,000 and 10,000. Preferably, the phosphonitrilic chloride pleionomers used herein are prepared by the process disclosed in Applicant's Copending Application entitled "Phosphonitrilic Chloride Pleionomers," Ser. No. 956,227 which was filed on Oct. 30, 1978 and which is incorporated herein as if fully set forth. That application discloses methods for the preparation of linear phosphonitrilic chloride pleionomers by heating phosphonitrilic chloride oligomers at temperatures of 275° to 350° C. for 1 to 20 hours while concurrently removing the phosphorus pentachloride vapors evolved. However, in its broadest aspect this invention is independent of the means employed to prepare the phosphonitrilic chloride pleionomers.

Preferably the pleionomers of this invention are admixed with a polyfunctional thiol (polythiol) or a polyfunctional acrylate (polyacrylate) or methacrylate (polymethacrylate) curing agent. These curing agents not only produce compositions which are curable and foamable at ambient temperatures, but they also have the effect of lowering the viscosity of the phosphazene. Because the desired viscosity of the curable and/or foamable compositions may vary according to the particular use or application for the composition, these curing agents can be used to temper the viscosity of the composition.

Polythiols which can be admixed with the phosphazenes of this invention are characterized by the general formula

where x is at least 2, and is preferably 2,3 or 4. While it is contemplated that polythiols represented by the formula wherein x is greater than 4 can be successfully employed in the practice of this invention, the di-, tri- and tetra-thiols and mixtures thereof are preferred. Examples of these preferred polythiols include ethanedithiol; n-butanedithiol; n-hexanedithiol, ethylene glycol dimercaptoacetate; ethylene glycol dimercaptopropionate; the polyethyleneglycol dimercaptoacetates, e.g., polyethyleneglycol di(3-mercaptopropionate); trimethylolethane tri(3-mercaptopropionate); pentaerythritol tetra(3-mercaptopropionate) and 2,2'-dimercaptodiethyl ether. The amount of the polythiol added will usually vary according to such considerations as the degree of crosslinking desired, the viscosity of the crosslinkable composition, and the rate of crosslinking desired during curing and/or foaming, among others. This amount generally falls within the range of from about 1 to about 25 parts per hundred parts (abbreviated phr) of the substituted phosphazene. Preferably the amount of polythiol incorporated into the compositions of this invention falls within the range of from about 5 to about 25 parts per hundred parts of phosphazene.

Polyacrylate or polymethacrylate curing agents used in this invention include, di-, tri- and tetra-funtional acrylates and methacrylates such as ehtylene dimethacrylate, trimethylolpropane triacrylate, and the like. The amount of polyfunctional acrylate or methacrylate used generally falls within the range of from about 1 to about 25 phr and preferably from 5 to 25 phr.

In still another preferred embodiment, the liquid phosphazenes of this invention, as well as compositions of these phosphazenes with a curing agent, are admixed with up to about 25 phr of a viscosity depressing agent. These compounds which increase the fluidity of the resulting composition, or, in other words, decrease the viscosity of the admixture. These compounds are liquid (preferably having a viscosity of less than 20 cps as measured at 23° C.) and compatible with the liquid phosphazene or compositions thereof—i.e., the viscosity depressant is inert to the phosphazene and its compositions. Examples of viscosity depressants include nitrobenzene, tetrahydronaphthalene, as well as various halo-substituted lower alkyl (having 1 to about 6 carbon atoms) substituted benzenes, trialkyl phosphates (the alkyl groups having 1 to about 6 carbon atoms), and tris-halo alkyl phosphates as long as the above criteria are met. Preferred viscosity depressants include tris-2-chloroethylphosphate, orthodichlorobenzene, monochlorobenzene, tri-n-butylphosphate, and toluene.

In some instances it may be desirable to increase the flame resistancy of the prepolymers of the present invention. Preferably this is accomplished by the use of a reactant capable of providing a brominated substituent (preferably a brominated aryl group) during the substitution reaction. Alternatively the desired amount of bromine may be incorporated into the already substituted prepolymer by methods known to the art such as by the use of a suitable brominating agent such as, for example, addition of elemental bromine to a portion of the ethylenically unsaturated groups.

The substituted prepolymers of the present invention as well as compositions thereof with curing agents and/or viscosity depressing agents are liquid at ambient temperatures and are useful in making cured elastomers, foams and coatings. Their liquid or fluid nature together with their ability to be cured and/or foamed at ambient temperatures render them attractive and convenient starting materials for making elastomers, foams and coatings possessing advantageous physical properties, for example, high resistance to flammability.

In a typical foaming process the liquid prepolymers of this invention are mixed with a curing agent, an appropriate initiator, a blowing agent and optionally a viscosity depressing agent. For example 100 parts of a prepolymer of this invention can be mixed with 10 parts of tris-(chloroethyl) phosphate, 10 parts of trimethylolethane tri-(3-mercaptopropionate), 2.5 parts of dichloracetic acid, 1 part of L-540 silicone surfactant (Manufactured by Union Carbide Company) and 10 parts of methylene chloride. Mixing is effected with a high speed mechanical stirrer until a substantially homogeneous mixture is obtained. At this point 0.6 parts of t-butyl perbenzoate (a crosslinking promoter) and 5 parts of 2-t-butylazo-2-hydroxybutane (a catalyst which serves the dual functions of a catalyst as well as acting as a blowing agent; when used together with an organic activator, it may be used alone or in combination with other blowing agents) are added to the mixture at room temperature—that is, without use of external heat. The resulting composition is stirred for an additional 30 to 60 seconds after which time the composition is allowed to rise and cure for 5 to 10 minutes, again without use of external heat.

Other initiators may also successfully be employed. For example free radical initiators of the peroxide-type such as benzoyl peroxide, cumene hydroperoxide, t-benzyl peroxyoctoate, acetyl peroxide, lauroyl peroxide, t-butyl, peroxyoctoate, methyl ethyl ketone peroxide and bis(1-hydroxy cyclohexyl) peroxide. Generally these initiators are used in amounts from about 0.1 to about 5 phr. Activators which may be employed with these initiators in foaming the prepolymers of this invention include cobalt octoate, N,N-dimethylaniline, N,N-diethylaniline, N,N-dimethyl toluidine and cobalt naphthenate. Other "azo-acid" systems such as dichloroacetic acid or other organic acids with 1-t-butylazo-1-hydroxycyclohexane, 1-t-butylazo-1-hydroxycyclopentane and 2-t-butylazo-2-hydroxy-5-methylhexane, and mixtures thereof may be used alone or in combination with other systems. Bicarbonates such as sodium bicarbonate, and other low boiling compounds such as trichlorofloromethane, pentane and the like can be used as blowing agents. These latter types of materials are generally used in amounts of from about 10 to about 40 phr.

In a typical procedure for curing the liquid prepolymers of this invention are mixed with up to 25 parts of a curing agent such as the mercaptans and the acrylates described above, a suitable amount of a crosslinking catalyst such as the peroxide type catalyst discussed above and optionally up to about 25 parts of a viscosity reducing agent. Generally up to about 5 parts of a peroxide catalyst is employed with the particular catalyst used varying according to the rate of cure desired in the composition, the cure temperature and other considerations. For example, when a quick cure at ambient temperatures is desired a fast acting catalyst is used (that is, one having a fast decomposition time); alternatively, when a longer room temperature is desired and/or when an elevated temperature is desired, a less active catalyst is generally employed so as to control the rate of cure. Other types of curing such as curing with actinic radiation, ultraviolet light, gamma rays, electron beams, etc., may be used. Other methods of chemical curing may also be used if desired. Elastomers having high resistance to flammability as well as having other desirable physical properties can be made accordingly.

While this invention has been discussed primarily in relation to substitution of chlorine atoms from linear phosphonitrilic chloride pleionomers, it will be understood that other linear phosphonitrilic halide pleionomers such as the bromides and chlorobromides can be used in the practice of this invention provided of course that such pleionomers have an average degree of polymerization of from about 20 to about 70.

Other modifications and variations of the present invention will now be readily apparent in light of the above teachings. It is therefore to be understood that changes may be made in particular embodiments described above which are within the spirit and intended scope of the invention as defined in the appended claims.

What is claimed is:

1. A liquid, linear, crosslinkable, substituted polymeric phosphazene having an average degree of polymerization of from about 20 to about 70 wherein substantially all of the substituents on said phosphazene are —OR, —SR, —NHR', —NR$_2$ or mixtures thereof in which R is an organic radical having no more than about 10 carbon atoms and R' is an organic radical having from 2 to about 10 carbon atoms; said phosphazene being further characterized in that from about 8% to about 50% of the total number of said substituents have at least one site of crosslinkable ethylenic unsaturation, in that at least 50% of said substituents are —OR groups, in that no more than 25% of said substituents are aromatic and in that said phosphazene has a viscosity of not more than 500,000 centipoises at 23° C.

2. A substituted polymeric phosphazene of claim 1 wherein the average degree of polymerization falls within the range of from about 20 to about 50.

3. A substituted polymeric phosphazene of claim 1 wherein the organic radicals of said substituents are open chain organic radicals.

4. A substituted polymeric phosphazene of claim 1 wherein from 8% to 25% of the substituents are diallylamino and 92% to 75% of the substituents are n-butoxy.

5. A substituted polymeric phosphazene of claim 1 wherein from 10% to 35% of the substituents are allyloxy and 90% to 65% of the substituents are n-butoxy.

6. A substituted polymeric phosphazene of claim 1 wherein from 10% to 35% of the substituents are methacryloyloxyethoxy and 90% to 65% of the substituents are n-butoxy.

7. A substituted polymeric phosphazene of claim 1 in admixture with up to about 25 phr of a polythiol curing agent.

8. A substituted polymeric phosphazene of claim 1 in admixture with up to about 25 phr of a polyacrylate or polymethacrylate curing agent.

9. A liquid polymeric phosphazene of claim 1 in admixture with up to about 25 phr of a viscosity depressing agent.

10. A process for the preparation of a liquid, linear crosslinkable substituted polymeric phosphazene comprising reacting in admixture (a) a linear phosphonitrilic chloride pleionomer having an average degree of polymerization of from about 20 to about 70, (b) an alkali metal alkoxide having up to about 10 carbon atoms in the molecule, (c) an alkali metal alkenoxide having up to about 10 carbon atoms in the molecule, and (d) optionally, an alkali metal phenoxide having up to about 10 carbon atoms in the molecule in amounts so that (i) said alkenoxide furnishes from about 8 to about 50% of the total number of substituents formed by replacement of chlorine from said pleionomer, (ii) no more than 25% of the substituents formed by replacement of chlorine from said pleionomer are furnished by said phenoxide, and (iii) the resultant phosphazene has a viscosity of no more than 500,000 centipoises at 23° C.

11. The process of claim 10 wherein the reactants consist of (a), (b), and (c) as therein set forth.

12. The process of claim 10 wherein the alkali metal of (b), (c), and (d) is sodium.

13. A process for the preparation of a liquid, linear crosslinkable, substituted polymeric phosphazene which comprises
  (1) reacting a linear phosphonitrilic chloride pleionomer having an average degree of polymerization of from about 20 to about 70 with a primary or a secondary alkenylamine each substituent of which has up to about 10 carbon atoms, in amounts so that from about 8 to about 50% of the chlorine atoms on said phosphonitrilic chloride pleionomer are replaced by an alkenylamino group thereby forming a partially substituted phosphonitrilic chloride pleionomer; and then
  (2) reacting said partially substituted phosphonitrilic chloride pleionomer with
    a. an alkali metal alkoxide having up to about 10 carbon atoms in the molecule, and
    b. optionally, an alkali metal phenoxide having up to about 10 carbon atoms in the molecule
  in amounts so that substantially all of the remaining chlorine atoms of said partially substituted phosphonitrilic chloride pleionomer are replaced by alkoxy and optionally, phenoxy groups, with the proviso that if an alkali metal phenoxide is employed no more than 25% of the chlorine atoms of the initial phosphonitrilic chloride pleionomer are replaced by phenoxy groups, and with the further proviso that the resultant fully substituted polymeric phosphazene has a viscosity of no more than 500,000 cps at 23° C.

14. The process of claim 13 wherein in step (2) the reactants consist of said partially substituted phosphonitrilic chloride pleionomer and said alakli metal alkoxide.

15. The process of claim 13 wherein the alkali metal of 2a and 2b is sodium.

16. A process for the preparation of a liquid, linear, crosslinkable substituted polymeric phosphazene which comprises
  (1) reacting in the presence of a tertiary amine a linear, phosphonitrilic chloride pleionomer having an average degree of polymerization of from about 20 to about 70 with a hydroxyalkyl acrylate or methacrylate having up to about 10 carbon atoms in the molecule or with an N-(hydroxyalkyl) acrylamide or methacrylamide having up to about 10 carbon atoms in the molecule in amounts so that from about 8 to about 50% of the chlorine atoms on said phosphonitrilic chloride pleionomer are replaced by acryloyloxyalkoxy or methacryloyloxy alkoxy groups or acryloylaminoalkoxy or methacryloylaminoalkoxy groups thereby forming a partially substituted phosphonitrilic chloride pleionomer; and then
  (2) reacting in the presence of a tertiary amine said partially substituted phosphonitrilic chloride pleionomer with
    a. an alkanol having up to about 10 carbon atoms in the molecule, and
    b. optionally, a phenol having up to about 10 carbon atoms in the molecule
  in amounts so that substantially all of the remaining chlorine atoms of aid partially substituted phosphonitrilic chloride pleionomer are replaced by alkoxy and optionally, phenoxy groups, with the proviso that if a phenol is employed no more than 25% of the chlorine atoms of the initial phosphonitrilic chloride pleionomer are replaced by phenoxy groups, and with the further proviso that the resultant fully substituted polymeric phosphasene has a viscosity of no more than 500,000 cps at 23° C.

17. The process of claim 16 wherein in step (2) the reactants consist of said partially substituted phosphonitrilic chloride pleionomer and said alkanol.

18. The process of claim 16 wherein in step (2) said pleionomer is reacted with an hydroxyalkyl methacrylate.

* * * * *

UNITED STATES PATENT AND TRADEMARK OFFICE
CERTIFICATE OF CORRECTION

PATENT NO. : 4,264,531

DATED : April 28, 1981

INVENTOR(S) : Hsueh M. Li et al

It is certified that error appears in the above—identified patent and that said Letters Patent is hereby corrected as shown below:

Column 4, line 55, reads "N-2-", should read -- N-(2- --.
Column 5, line 55, reads "a suitable insert", should read -- a suitable inert --.
Column 8, line 39, reads "paste-like diallyalmino", should read -- paste-like diallylamino --.
Column 10, line 21, reads "such as ehtylene", should read -- such as ethylene --.
Column 11, line 56, reads "temperature is", should read -- temperature cure is --.
Column 11, line 57, reads "temperature is desired", should read -- temperature cure is desired --.
Column 14, line 29, reads "atoms of aid", should read -- atoms of said --.
Column 14, line 36, reads "phosphasene", should read -- phosphazene --.
Column 14, line 41, Claim 18, reads "step (2)", should read -- step (1) --.

Signed and Sealed this

Seventeenth Day of November 1981

[SEAL]

Attest:

GERALD J. MOSSINGHOFF

Attesting Officer    Commissioner of Patents and Trademarks